US00PP17283P2

(12) United States Plant Patent
Jordan et al.

(10) Patent No.: US PP17,283 P2
(45) Date of Patent: Dec. 19, 2006

(54) ***CYNARA* PLANT NAMED '22BD'**

(50) Latin Name: *Cynara scolymus*
Varietal Denomination: 22BD

(75) Inventors: John Jordan, Brawley, CA (US); Stephen Jordan, Lompoc, CA (US)

(73) Assignee: Big Heart Seed, Brawley, CA (US)

( * ) Notice: Subject to any disclaimer, the term of this patent is extended or adjusted under 35 U.S.C. 154(b) by 0 days.

(21) Appl. No.: 11/263,784

(22) Filed: Oct. 31, 2005

(51) Int. Cl.
*A01H 5/00* (2006.01)

(52) U.S. Cl. ..... Plt./258

(58) Field of Classification Search ..... Plt./258
See application file for complete search history.

*Primary Examiner*—Anne Marie Grunberg
*Assistant Examiner*—Annette H Para
(74) *Attorney, Agent, or Firm*—Townsend and Townsend and Crew LLP

(57) ABSTRACT

A new and distinct variety of *Cynara* named '22BD' that is characterized by upright habit, deeply fluted hairy stems, large ascending leaves, and edible compact immature flower buds that are uniform in shape and color.

6 Drawing Sheets

Botanical designation: *Cynara scolymus*.
Variety denomination: '22BD'.

BACKGROUND OF THE INVENTION

The present invention comprises a new and distinct cultivar of artichoke plant, a perennial herb that is grown as a food crop for the production of edible vegetable delicacies. The new cultivar is known botanically as *Cynara scolymus* and is herein referred to by the cultivar name '22BD'.

The new *Cynara scolymus* cultivar, named '22BD', is a member of the family Compositae, also known as Asteraceae. An individual whole plant of '22BD' comprises a main stem, lateral stems, leaves, and immature flower buds known as involucra. The edible parts of freshly harvested immature flower buds comprise inner and outer bracts, stem, and parts of the fleshy receptacle. If permitted to mature, the immature flower buds will develop into large mature flower heads known as capitula.

'22BD' is the product of a formal breeding program conducted by the inventor in cultivated areas of Brawley, Calif. and Lompoc, Calif. The purpose of the breeding program is to produce new artichoke plants that are grown to yield edible immature flower buds of improved taste, using simplified propagation methods.

The New cultivar named '22BD' was selected in 2000 by the inventor in Brawley, Calif. In brief, '22BD' was isolated from an individual crop of open-pollinated *Cynara scolymus* '9bdg' (unpatented) seedlings. It was selected as a single plant based on the criteria of purple color, striking appearance, and compact form, as well as the uniform and consistent appearance when asexually propagated.

The closest prior art known to the inventor is the parent plant. The female and male parent are *Cynara scolymus* '9bdg' (unpatented). '22BD' is distinguishable from *Cynara scolymus* '9bdg' by ascending leaves, uniform seeds, productivity of buds, and uniform, consistent purple-green color of buds. The color consistency and intensity is strikingly different from the '9bdg' parents and other crosses. The parent '9bdg' exhibits arched leaves, as well as variability in color and productivity of progeny.

The instant plant of '22BD' that was selected and grown in Brawley, Calif., was transported to a cultivated area of Lompoc, Calif., and first asexually propagated by the inventor in 2002. The method used for the first asexual propagation was division. Later plants were transported to a laboratory and asexually propagated by tissue culture. The distinguishing characteristics of the new *Cynara scolymus* cultivar named '22BD' have been determined to be stable, fixed, where it was reproduce true to type in successive generations.

Brawley is located in California's Imperial Valley in Imperial County. It is a low desert climate. Lompoc is located on California's central coast in Santa Barbara County. Conditions in Lompoc vary in the summer months. Air temperatures range from 60° Fahrenheit to 80° Fahrenheit. The relative humidity is generally high. Prevailing winds are northwesterly and rainfall averages 12-inches per year. The well-draining fertile soil is clay, loam, acid or alkaline, with regular to heavy watering, and full sun.

BRIEF SUMMARY OF THE INVENTION

The following traits have been repeatedly observed and represent the characteristics of the *Cynara scolymus* cultivar '22BD'. These combinations of traits distinguish '22BD' from all other commercial cultivars of *Cynara* known to the inventor. '22BD' has not been tested under all possible conditions and phenotypic differences may be observed with variations in environmental, climatic, and cultural conditions such as temperature, humidity, light intensity, and day length, without however, any variance in genotype. *Cynara scolymus* '22BD' exhibits upright habit; deeply fluted hairy stems; and large ascending leaves. *Cynara scolymus* '22BD' is productive, consistently yielding 30–40 immature flower buds per plant. The immature flower buds are compact and uniform in shape and color.

*Cynara scolymus* '22BD' produces uniform seed and is asexually propagated by methods of tissue culture and division. The immature flower buds are typically harvested from March to November. *Cynara scolymus* '22BD' is hardy to USDA Zone 6.

The immature flower buds exhibit firm bracts, stem and receptacle, mild flavor, and tender consistency. It takes approximately 5 to 9 months to produce a harvestable crop of edible immature flower buds. The plants are susceptible to aphids, nematodes, powdery mildew and leaf spot.

BRIEF DESCRIPTION OF THE DRAWINGS

The accompanying photographic drawings FIG. 1, FIG. 2, FIG. 3, FIG. 4, FIG. 5, and FIG. 6 illustrate the overall appearance of the new *Cynara scolymus* variety '22BD'. The photographs were obtained in June 2005 in Lompoc, Calif. from field grown plants that were 6-months-old at the time. All photographs are taken using conventional techniques and although foliage colors may appear different from actual colors due to light reflectance, they are as accurate as possible by conventional photography. Colors in the drawings may differ from the color values cited in the detailed botanical description which accurately describe the actual colors of the new cultivar '22BD' named herein.

FIG. 1 depicts an individual field grown plant from a side perspective illustrating habit and buds.

FIG. 2 depicts a close-up view of buds on a grown plant.

FIG. 3 depicts a close-up view of an individual harvested immature flower bud illustrating the outside of a whole bud and a cross-section of a halved bud.

FIG. 5 depicts a top view of a single bud.

FIG. 6 depicts a side view of an individual harvested bud, including its stem.

DETAILED DESCRIPTION OF THE INVENTION

Figure 1:
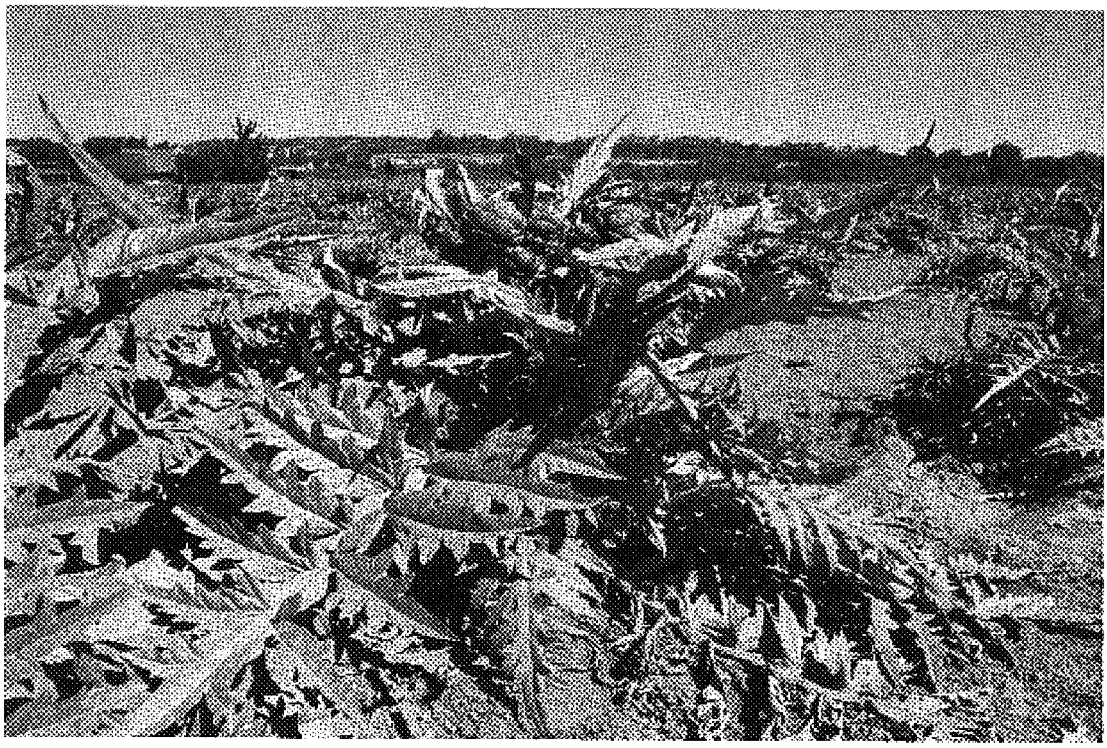
Figure 2:
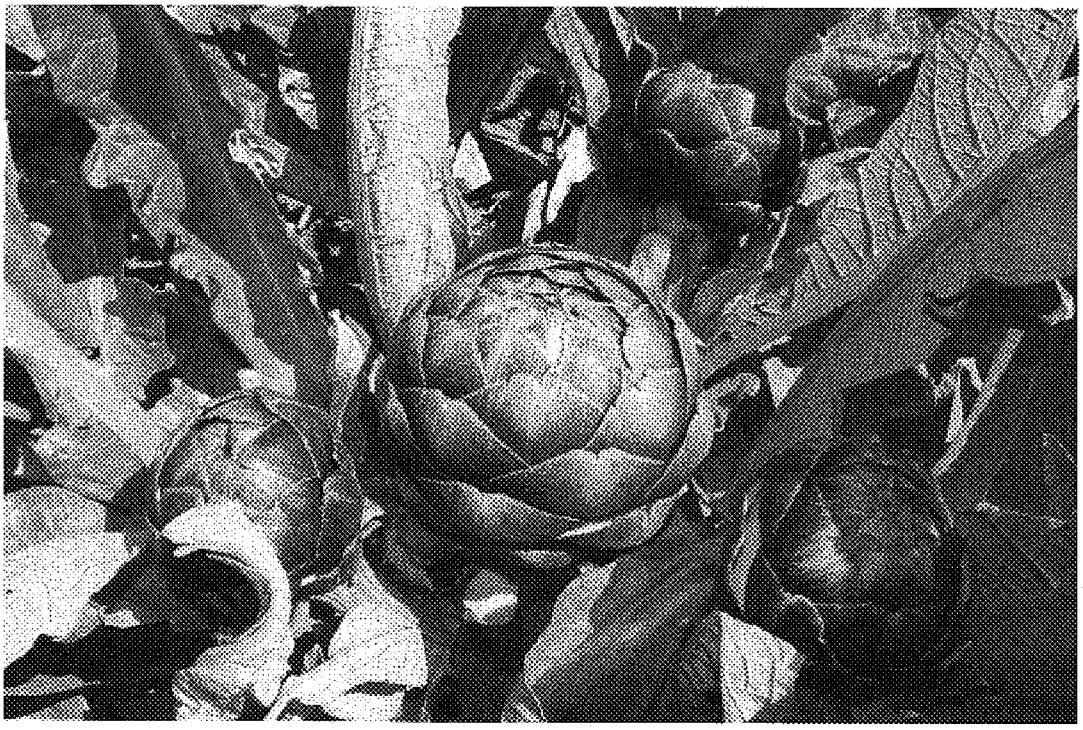
Figure 3:
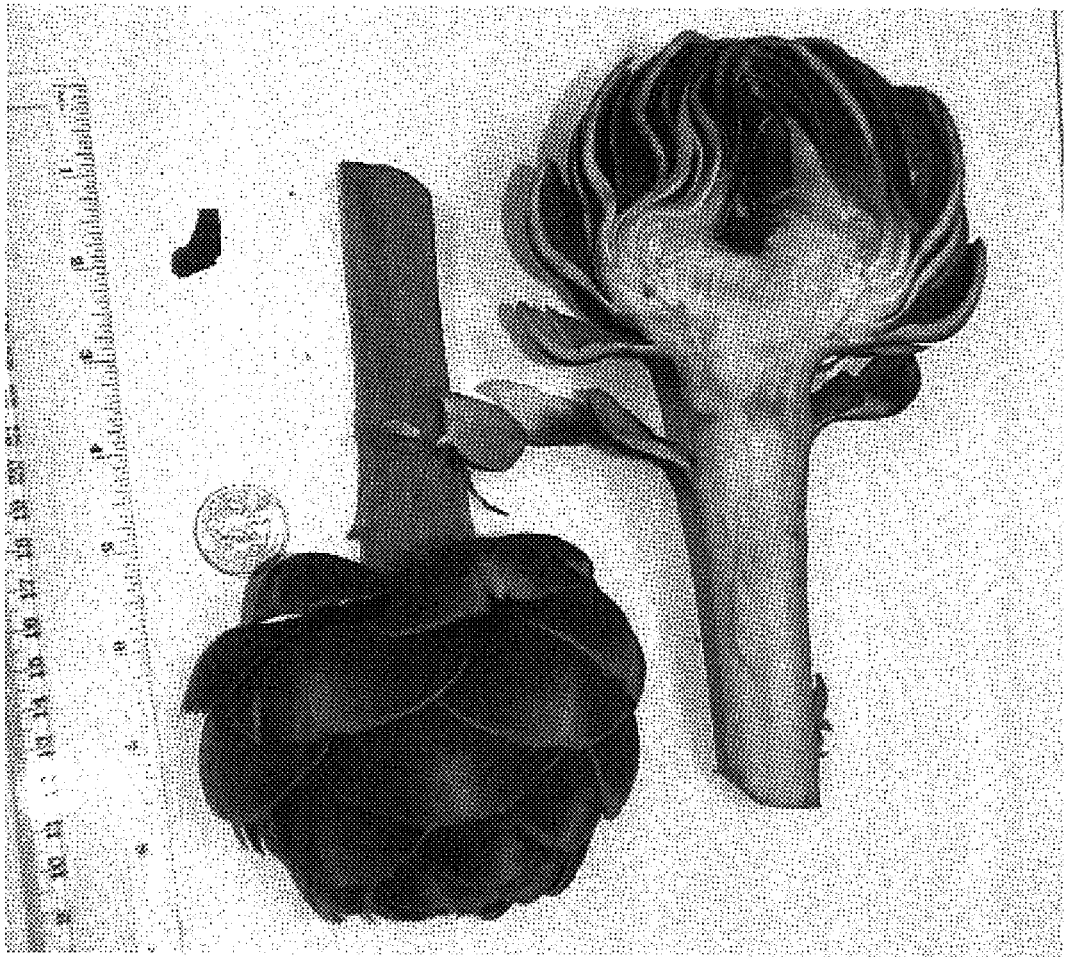
Figure 4A:
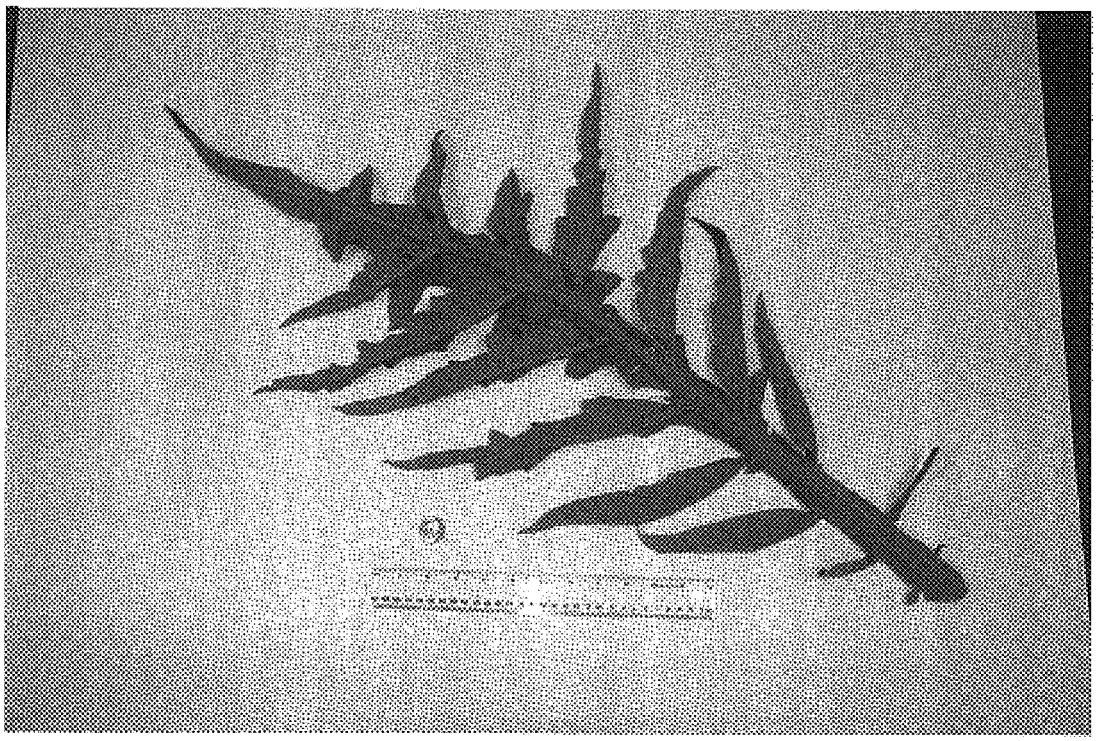
FIG. 4A and FIG. 4B depict leaves from a mature '22BD' plant.
Figure 4B:
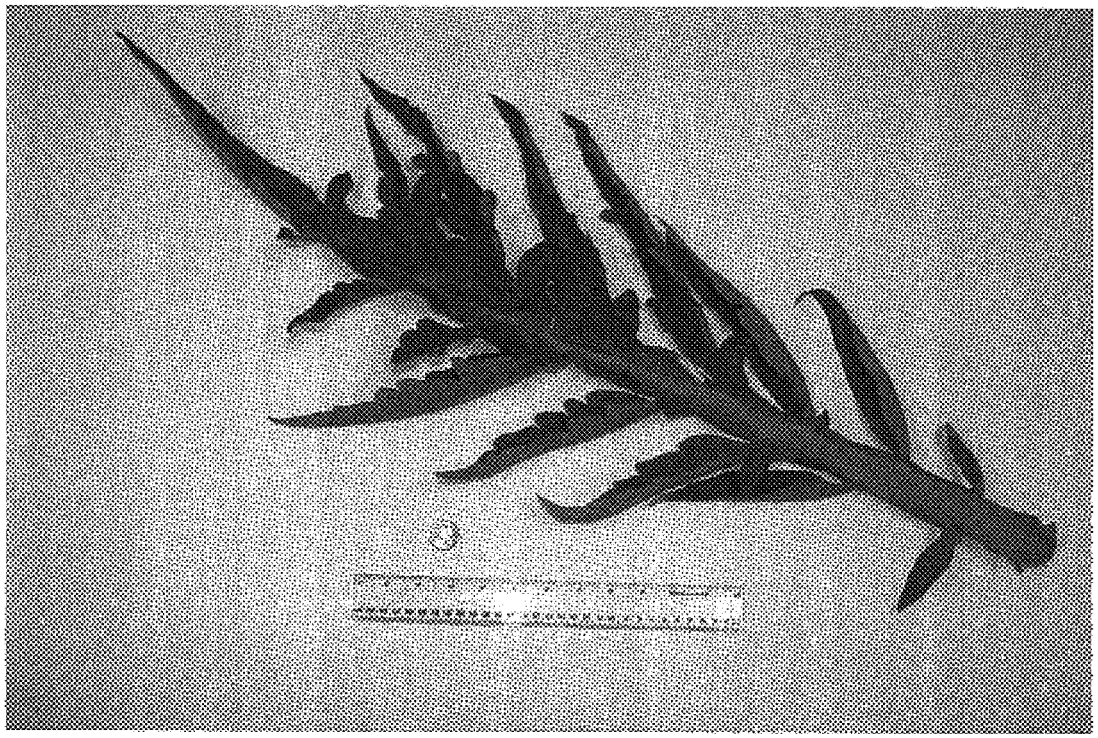
Figure 5:
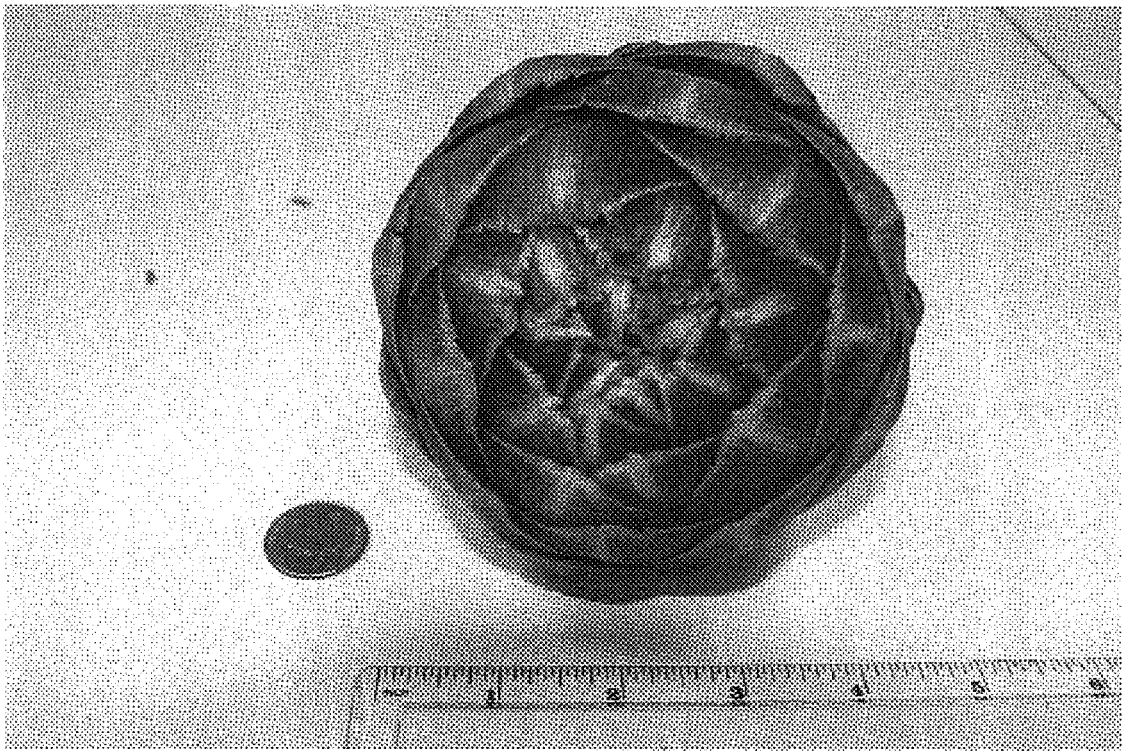
Figure 6:
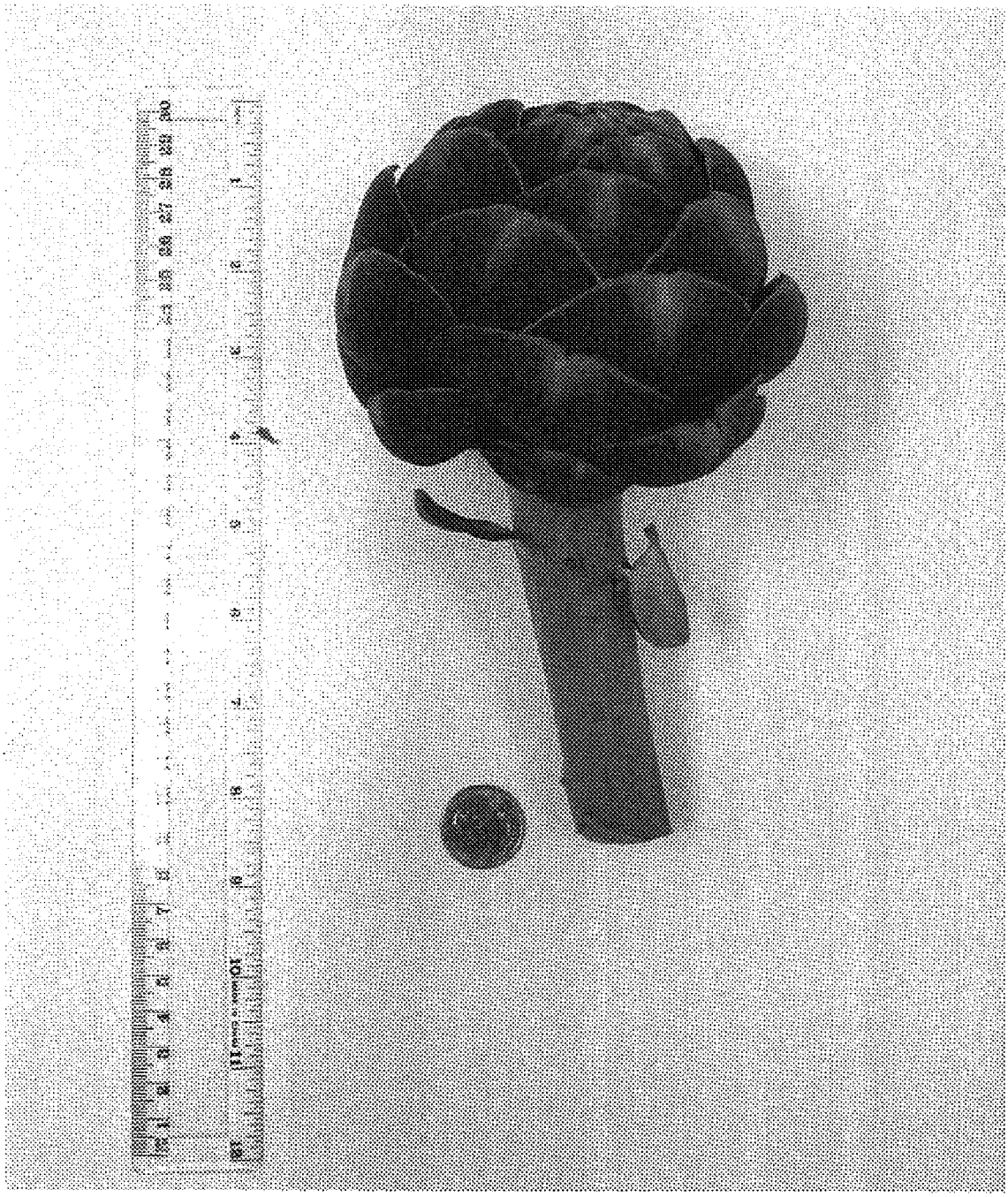

The following observations, measurements and values describe the new cultivar '22BD' as grown in Lompoc, Calif. under conditions used in horticultural practice. The plants were grown in rows where row spacing (bed centers) was at 2 meters and individual plant spacing at 90 cm. Data was collected in June and October of 2005 from plants that were 9 and 6-months-old, both field grown in full sun. The growing requirements are similar to that of other species. Color determinations are in accordance with the 2001 edition of The Royal Horticultural Society Colour Chart of London, England.

General:

*Plant parentage.*—*Cynara scolymus* '22BD' is a single plant selection from a group of open-pollinated plants of the following parentage: Female parent: *Cynara scolymus* '9bdg' (unpatented). Male parent: *Cynara scolymus* '9bdg' (unpatented).

*Plant habit.*—Upright habit with vertical and semi-vertical stems.

*Plant vigor.*—Vigorous.

*Plant type.*—Perennial herb.

*Plant height* (*at time of harvest*).—Average of 1 meter, 22 cm.

*Plant width* (*at time of harvest*).—Average of 2 meters, 15 cm.

*Root system.*—Thick and fibrous.

*Plant propagation.*—Asexual plant propagation is accomplished by the methods of tissue culture and division.

Stem:

*Branching habit.*—Basal branching and caulescent branching are individually present.

*Main stem height.*—Average of 60 cm.

*Main stem diameter.*—Average of 5 cm.

*Lateral stem aspect.*—Assurgent.

*Quantity of lateral stems.*—Average of 8 lateral stems per individual plant.

*Lateral stem length.*—Approximately 10 cm to 30 cm on an individual plant.

*Lateral stem diameter.*—Approximately 1.50 cm to 2.25 cm on an individual plant.

*Stem surface* (*main and lateral stems*).—Combination of deeply fluted and tomentose.

*Color of tomenta.*—198D.

*Stem shape* (*main and lateral stems*).—Columnar in shape.

*Stem strength* (*main and lateral stems*).—Strong and rigid.

*Stem colors* (*main and lateral stems*).—N186C, 138A, 138B and 138C are individually present.

*Lateral stem angle at emergence.*—Average angle of 50° on an individual plant.

*Internode length.*—Approximately 1.7 cm to 9 cm on an individual plant.

Foliage:

*Foliage type.*—Evergreen.

*Leaf arrangement.*—Alternate arrangement.

*Leaf division.*—Simple.

*Leaf margin.*—Cleft.

*Leaf density.*—Approximately 10 to 20 leaves on an individual stem.

*Leaf shape.*—Closest to a combination of lacerate and laciniate in shape.

*Leaf apex.*—Acute.

*Leaf base.*—Truncate base that is sulcate in cross-section.

*Leaf attachment.*—Decurrent.

*Leaf color* (*abaxial surface*).—194B and 183C are individually present.

*Leaf color* (*adaxial surface*).—191A and 183C are individually present.

*Leaf appearance* (*abaxial surface*).—Dull appearance.

*Leaf appearance* (*adaxial surface*).—Dull appearance.

*Leaf texture.*—Rough and hairy.

*Leaf venation pattern.*—Penniveined pattern with mid-vein depressed on the adaxial surface and prominently protruding on the abaxial surface.

*Vein color* (*abaxial surface*).—194B and 144C.

*Vein color* (*adaxial surface*).—197D and 194C.

*Leaf surface* (*abaxial surface*).—Tomentose.

*Leaf surface* (*adaxial surface*).—Tomentulose.

*Color of tomenta.*—198D.

*Length of leaf.*—Average of 99 cm.

*Width of leaf.*—Average of 74 cm.

*Quantity of lobes on leaf.*—Approximately 7 to 14 lobes per individual leaf.

*Lobe apex.*—Obtuse apex to rounded apex to acute apex on an individual leaf.

*Lobe length.*—Approximately 20 cm to 37 cm on an individual leaf.

*Lobe width.*—Approximately 5.50 cm to 16 cm on an individual leaf.

*Leaf fragrance.*—No fragrance is observed.
*Angle of leaf to stem.*—Approximately 45° angle to an individual stem.

Immature flower bud (involucrum):
*Bud shape* (*involucrum shape*).—Closest to oblate in shape.
*Bud apex* (*involucrum apex*).—Closest to obtuse apex.
*Bud base* (*involucrum base*).—Closest to rounded base.
*Bud form* (*involucrum form*).—Compact form.
*Bud texture* (*involucrum texture*).—Hard and smooth.
*Bud surface* (*involucrum surface*).—Glabrous.
*Bud height* (*involucrum height*).—Approximately 5 cm to 12.50 cm on an individual plant.
*Bud diameter* (*involucrum diameter*).—Approximately 7 cm to 13 cm on an individual plant.
*Quantity of buds* (*involucre quantity*).—Approximately 4 to 6 per individual stem, or 30 to 40 per individual plant.
*Bract arrangement.*—Imbricate.
*Quantity of outer bracts.*—Average of 75 individual outer bracts per individual immature flower bud.
*Quantity of inner bracts.*—Average of 100 individual inner bracts per individual immature flower bud.
*Bract texture* (*inner and outer bracts*).—Smooth.
*Outer bract apex.*—Combination of spinescent and retuse is present on an individual outer bract apex.
*Apical spine shape.*—Triangular in shape.
*Apical spine color.*—199A.
*Apical spine dimensions.*—Average of 4.00 mm in height and 1.00 mm in width.
*Inner bract apex.*—Acute.
*Outer bract base.*—Truncate.
*Inner bract base.*—Truncate.
*Bract margin* (*inner and outer bracts*).—Entire.
*Outer bract surfaces* (*ventral and dorsal surfaces*).—Glabrous.
*Inner bract surfaces:* (*ventral and dorsal surfaces*).—Glabrous.
*Outer bract shape.*—Closest to ovate and slightly involuted.
*Inner bract shape.*—Closest to oblong.
*Outer bract length.*—Approximately 6.00 cm to 7.00 cm in length on an individual immature flower bud.
*Outer bract width.*—Approximately 3.50 cm to 6.00 cm in width on an individual immature flower bud.
*Inner bract length.*—Approximately 5.50 cm to 7.25 cm in length on an individual immature flower bud.
*Inner bract width.*—Approximately 1.25 cm to 2.50 cm in width on an individual immature flower bud.
*Outer bract colors* (*ventral and dorsal surfaces*).—183B and 191A.
*Inner bract colors* (*ventral and dorsal surfaces*).—191B and 191C.
*Receptacle shape.*—Closest to concavo-convex in shape.
*Receptacle dimensions.*—Averages 1.75 cm in thickness and 6.50 cm in diameter.
*Receptacle color.*—160D.
*Receptacle texture.*—Smooth.
*Pappus color.*—159C.
*Pappus dimensions.*—Less than 0.25 mm in diameter and 4.00 cm in length.
*Pappus quantity* (*number of bristles*).—500+.
*Pappus shape* (*individual bristle shape*).—Filament in shape.
*Pappus texture.*—Silky in texture.
*Duration of cold storage.*—3 to 7 days.
*Cold storage temperature.*—34° Fahrenheit.
*Cold storage response.*—Slight fading of purple color after seven days and minor stem cut discoloration.
*Shelf life.*—A range of 3–5 days shelf life.

Mature flower head (capitulum):
*Infloresence type.*—Capitulum.
*Persistent or self-cleaning.*—Persistent.
*Fragrance.*—Slightly tangy with sweet overtones.
*Inflorescence shape.*—Closest to oblate in shape.
*Inflorescence appearance.*—Thistle-like in appearance.
*Inflorescence diameter.*—Average of 14 cm on an individual plant.
*Inflorescence depth.*—Average of 13 cm.
*Peduncle shape.*—Columnar in shape.
*Peduncle length.*—Approximately 11 cm to 15 cm on an individual plant.
*Peduncle diameter.*—Approximately 1.00 cm to 1.75 cm on an individual plant.
*Peduncle color.*—194B, 191A, 187A, and N187B are individually present.
*Peduncle surface.*—Combination of deeply fluted and tomentose.
*Color of tomena.*—198D.
*Peduncle strength.*—Strong.
*Peduncle texture.*—Rigid, ribbed, and hairy.
*Quantity of outer bracts.*—Average of 75 outer bracts per individual mature flower head.
*Quantity of inner bracts.*—Average of 100 inner bracts per individual mature flower head.
*Outer bract shape.*—Closest to ovate in shape and slightly involute in cross-section.
*Inner bract shape.*—Closest to oblong in shape.
*Outer bract width.*—Approximately 5.00 cm to 6.75 cm.
*Outer bract length.*—Approximately 6.50 cm to 8.50 cm.
*Inner bract width.*—Approximately 2.00 cm to 3.50 cm.
*Inner bract length.*—Approximately 5.25 cm to 7.00 cm.
*Bract margin* (*inner and outer bracts*).—Mostly entire.
*Outer bract apex.*—Combination of spinescent and retuse is present on an individual outer bract apex.
*Apical spine* (*per outer bract*).—1 per individual outer bract.
*Apical spine height.*—Approximately 1.00 mm to 4.00 mm on an individual outer bract.
*Apical spine width.*—Approximately 0.50 mm to 1.00 mm on an individual outer bract.
*Apical spine shape.*—Triangular in shape.
*Apical spine color.*—199A and 187A are individually present.
*Inner bract apex.*—Acute.
*Bract base* (*inner and outer bracts*).—Truncate base.
*Inner bract color* (*dorsal surface*).—160D.
*Inner bract color* (*ventral surface*).—160D.
*Outer bract color* (*dorsal surface*).—187A and 138B are individually present.
*Outer bract color* (*ventral surface*).—187A and 138B are individually present.
*Inner and outer bract surfaces* (*dorsal surfaces*).—Glabrous.
*Inner and outer bract surfaces* (*ventral surfaces*).—Glabrous.
*Inner and outer bract textures.*—Smooth.

*Disk florets.*—200+.
*Corolla color.*—79D and 162A are individually present.
*Corolla dimensions.*—Average of 2 mm in diameter and 2 cm in length.
*Petals.*—Average of 5 in number.
*Petal shape.*—Closest to oblong.
*Petals fused or unfused.*—Fused.
*Petal apex.*—Rounded apex.
*Petal base.*—Truncate base.
*Petal color.*—79D.
*Pappus quantity* (*number of individual bristles*).—500+.
*Pappus color.*—159C.
*Pappus appearance.*—Iridescent.
*Pappus texture.*—Silky in texture.
*Pappus shape* (*individual bristle shape*).—Plumose.
*Pappus dimensions* (*individual bristle*).—Average of 4.75 cm in length and less than 0.50 mm in diameter.
*Receptacle thickness.*—Average of 3.50 cm.
*Receptacle diameter.*—Average of 9.50 cm.
*Receptacle shape.*—Closest to concavo-convex.
*Receptacle colors.*—159C and 165A are individually present.

Reproductive organs:
*Stamens.*—7 in number adnate to corolla.
*Stamen color.*—79D.
*Stamen length.*—Average of 2.00 cm.
*Stamen diameter.*—Average of less than 0.25 mm.
*Anther.*—Connate to stamen.
*Anther color.*—N87C.
*Pollen amount.*—Low.
*Pollen color.*—79C.
*Pistil.*—One in number.
*Pistil shape.*—Filament in shape.
*Pistil surface.*—Glabrous.
*Pistil color.*—79C.
*Pistil length.*—Average of 6.00 cm.
*Pistil diameter.*—Average of less than 0.50 mm.
*Stigma color.*—79C.
*Stigma dimensions.*—Average of less than 0.75 mm in diameter and 2.00 mm in length.
*Stigma shape.*—Filament.
*Stigma surface.*—Glabrous.
*Ovary number.*—200+ in number per individual mature flower head.
*Ovary position.*—Inferior.
*Ovary color.*—159C and 165A are individually present.
*Ovary shape.*—Oval.
*Ovary dimensions.*—Average of 0.25 cm in width and 0.50 cm in height.

Seed:
*Shape of seed.*—Closest to ovoid.
*Seed surface.*—Glabrous.
*Seed length.*—Average of 0.75 cm.
*Seed diameter.*—Average of 0.50 cm.
*Seed apex.*—Closest to acute.
*Seed base.*—Closest to rounded.
*Seed color.*—158B, N200C, and 202A are individually present.
*Number of seeds.*—Average of 200+ seeds in number, and mostly produced by the primary mature flower head and 3 secondary mature flower heads combined.
*Seed appearance.*—Semi-glossy.

What is claimed is:

1. A new and distinct variety of artichoke plant having the characteristics essentially as described and illustrated herein.

* * * * *